United States Patent [19]

O'Dwyer

[11] Patent Number: 5,977,555
[45] Date of Patent: Nov. 2, 1999

[54] METHOD AND APPARATUS FOR DETECTING CRACKS IN A FLIP-CHIP DIE USING PASSIVE SCANNING-HEAD MICROSCOPY

[75] Inventor: Kevin O'Dwyer, Sugar Land, Tex.

[73] Assignee: Texas Instruments Incorporated, Dallas, Tex.

[21] Appl. No.: 08/992,705

[22] Filed: Dec. 17, 1997

Related U.S. Application Data

[60] Provisional application No. 60/033,100, Dec. 17, 1996.

[51] Int. Cl.[6] .................................................. G01N 29/24
[52] U.S. Cl. ...................... 250/559.45; 250/307; 250/234
[58] Field of Search ........................... 250/216, 234–236, 250/306, 307, 559.45, 559.46, 559.48; 73/634, 618

[56] References Cited

U.S. PATENT DOCUMENTS 5,431,055  7/1995  Takata et al. ............................ 250/307

*Primary Examiner*—Stephone Allen
*Attorney, Agent, or Firm*—Robert D. Marshall, Jr.; Gerald E. Laws; Richard L. Donaldson

[57] ABSTRACT

An apparatus for detecting cracks in a flip-chip die which comprises an emitter (2) coupled to the die (1) for emitting energy along an axis, a probe (3) located on the die for receiving the energy, and a device (19) coupled to the probe for detecting the energy along the axis.

18 Claims, 2 Drawing Sheets

METHOD AND APPARATUS FOR DETECTING CRACKS IN A FLIP-CHIP DIE USING PASSIVE SCANNING-HEAD MICROSCOPY

This application claims priority under 35 USC 119 (e) (1) of provisional application Ser. No. 60/033,100, filed Dec. 17, 1996.

TECHNICAL FIELD OF THE INVENTION

This invention relates generally to the field of integrated circuit manufacture, and more particularly, to a method and apparatus for detecting cracks in a flip-chip die using passive scanning-head microscopy.

BACKGROUND OF THE INVENTION

During the manufacture of flip-chip dies, it is important to detect fine cracks in these dies, including vertical cracks. These cracks can form during the making of the die itself, or during the removal process when separating the die from a ceramic substrate. Standard acoustic microscopy has been used in the past in an attempt to detect these cracks. However, because standard acoustic microscopy uses only planar waves from above the sample which are traveling downward, vertical cracks in a die might be impossible to detect, as they may have little or no cross-sectional area in the z-axis.

Another problem that exists is the construction of the transducer. Because the transducer must be capable of both transmitting and receiving acoustic energy signals in a single device, this leads to increased complexity and costs during its manufacture. Also, because the flip-chip dies are often encapsulated with a plastic or other material which have differing acoustic energy velocities, usually at least two different frequencies of acoustic energy are propagated during the testing process. Further, because the size of a flip-chip die is steadily decreasing, and with it a need to detect smaller and smaller cracks, this leads to a requirement for higher level frequencies of acoustic energy for testing. These factors all contribute to increased costs for the manufacture of transducers that possess the necessary capabilities.

SUMMARY OF THE INVENTION

Therefore, a need has arisen for an improved method and apparatus for detecting flip-chip die cracks. A further need exists for a method and apparatus for detecting flip-chip die cracks that reduce both the complexity and the cost of the manufacturing process.

In accordance with the present invention, a method and apparatus are provided that use passive scanning-head microscopy to detect cracks in flip-chip dies and which substantially eliminate or reduce disadvantages and problems associated with previously developed methods. The invention features an apparatus for detecting cracks in a flip-chip die which comprises an emitter for emitting energy along an axis, a probe located on the die for receiving the energy, and a device coupled to the probe for detecting the energy along the axis. More specifically, the energy comprises acoustic energy or laser light energy. The acoustic energy can be transmitted in compression wave pulses or in continuous waves. Further, in one embodiment, the emitter emits energy along a second axis and a third axis which are perpendicular to each other and to the original axis, and the device can detect energy in these axes.

In another embodiment, the device for detecting the energy comprises a filter for processing the energy into various sections of the frequency spectrum and an analog to digital converter for converting the energy from an analog form into a digital signal. The emitter comprises a controller for controlling the amplitude, timing, frequency and phase of the energy. Furthermore, in another embodiment, the present invention further comprises a display coupled to the device for detecting the energy for presenting visual images of the energy.

In accordance with another aspect of the present invention, there is provided a method for detecting flip-chip die cracks which comprises the steps of emitting energy from an emitter coupled to the die along an axis, receiving the energy with a probe located on the die, and detecting the energy with a device coupled to the probe along the axis. The method further comprises the steps of emitting energy from the emitter along a second axis and a third axis which are perpendicular to each other and to the original axis, receiving the energy with the probe along the second axis and the third axis, and detecting the energy with a device along the second axis and the third axis. The energy comprises acoustic energy that is transmitted in either compression wave pulses or continuous waves.

A technical advantage of the method detecting flip-chip die cracks is that it allows up to 3-axis vibration, as well as up to 3-axis passive pickup of acoustic energy. The emitter can output transverse waves in the x or y direction and also longitudinal waves in the z axis. The detector can pick up vibrations in all three axes, allowing sensitivity to cracks in the x, y or z planes. Thus, a more precise localization of defects can be made.

Another technical advantage is that the emitter and the probe for receiving energy are separated, which reduces the complexity of the manufacturing process because small transducers must contain both components together.

BRIEF DESCRIPTION OF THE DRAWINGS

For a more complete understanding of the present invention, the objects and advantages thereof, reference is now made to the following description taken in conjunction with the accompanying drawings in which like reference numbers indicate like features and wherein.

DETAILED DESCRIPTION OF THE INVENTION

Preferred embodiments of the present invention are illustrated in the FIGURES, like numeral being used to refer to like and corresponding parts of the various drawings.

Figure 1:
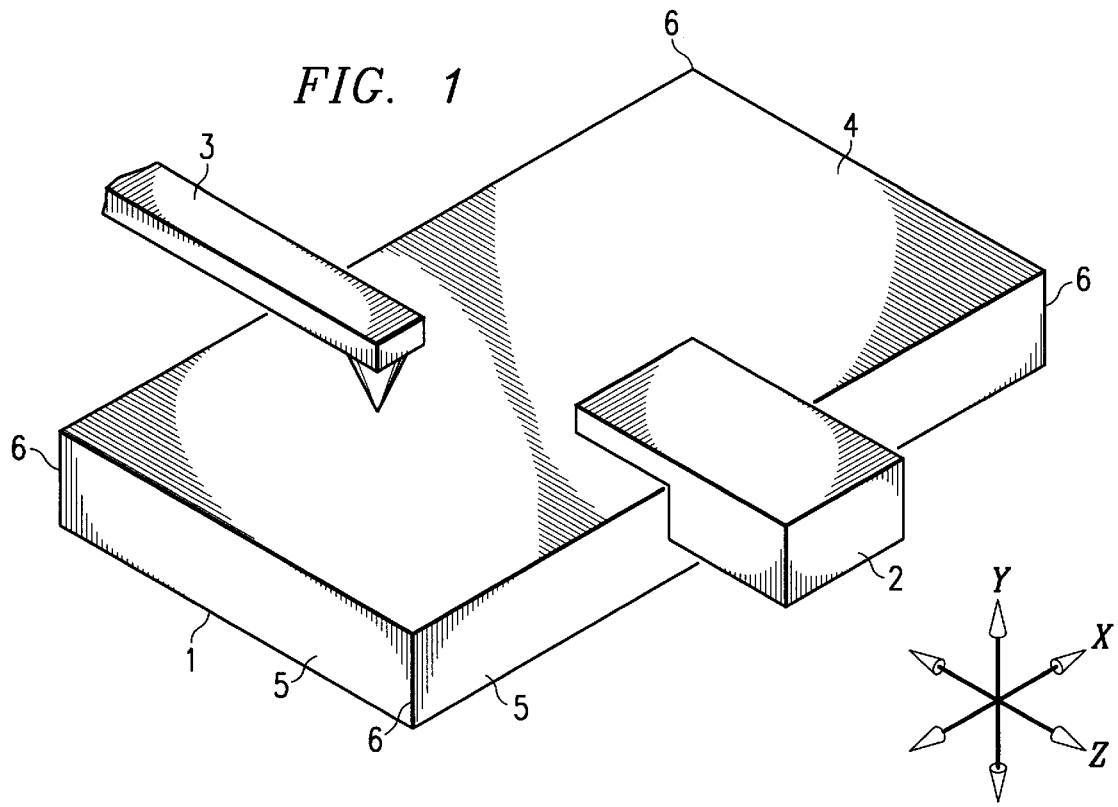
FIG. 1 is a simplified pictorial view of the apparatus for detecting flip-chip die cracks.

FIG. 1 shows the apparatus for detecting cracks in a flip-chip die. Chip 1 is an ordinary silicon wafer chip, which is typically less than 20 mils thick. While chip 1 might be attached to a circuit board or ceramic coupon, or be encapsulated with a plastic coating, this would not effect the accuracy of the present invention.

During the manufacturing process of a chip, vertical cracks can form. However, these cracks are often difficult to detect because the cross-sectional area is often extremely small. Therefore, this invention solves this problem by presenting an accurate, cost-effective apparatus and method of detecting these cracks.

Emitter 2 is connected to chip 1. Emitter 2 produces acoustic energy which is transmitted through chip 1. Emitter 2 is capable of directing energy in all three axes: x, y, and z. Emitter 2 transmits the acoustic energy through chip 1, where it is then received by scanning pickup probe 3. In this embodiment, scanning pickup probe 3 is similar in theory of operation to a phonographic needle used by turntables to play vinyl phonographic records. Scanning pickup probe 3 is capable of movement across the entire top portion of chip 1. Emitter 2 can be attached at any side 5 or corner 6 of chip 1 in order to transmit the acoustic energy. Scanning pickup probe 3 is always in contact with some portion of chip top 4. Scanning pickup probe 3 can scan in various patterns, including moving in a straight line, or scanning in a raster pattern.

Figure 2A:
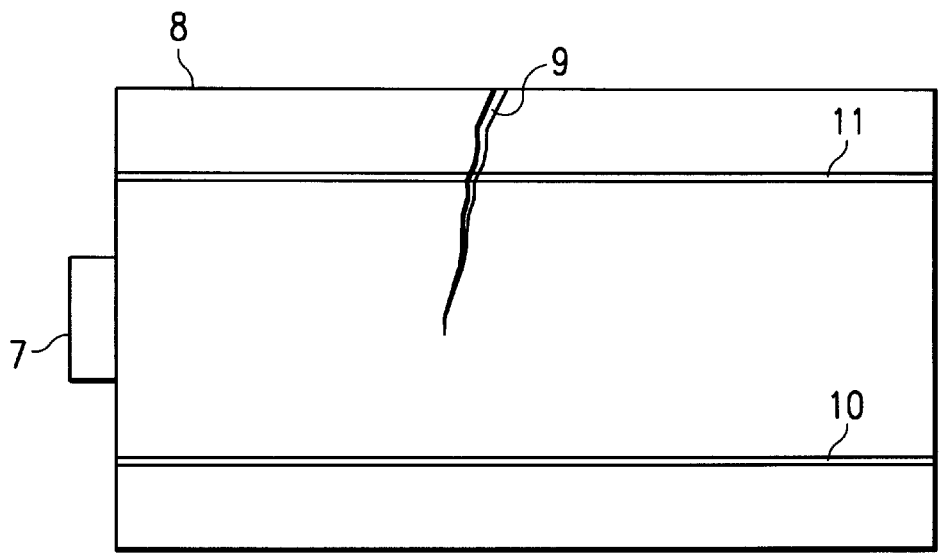
FIG. 2A is a top pictorial view of a flip-chip die.
Figure 2B:
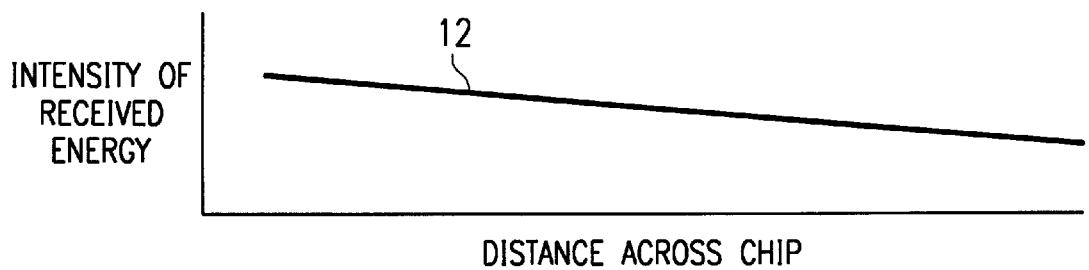
FIGS. 2B & 2C graphically illustrate the intensity of received acoustic energy versus distance.
Figure 2C:
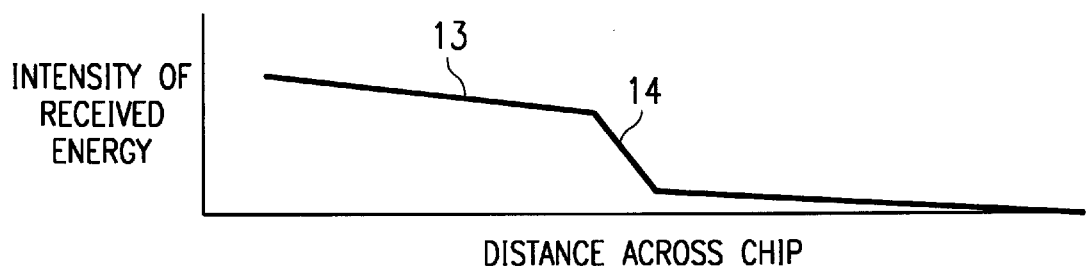

FIGS. 2A, 2B & 2C show the effect of the received acoustic energy on the system that is caused by a crack in the flip-chip die. In FIG. 2A, vertical crack 9 is shown in the top of chip 8. Also shown is one position for emitter 7. Lines 10 & 11 represent two possible pathways for the scanning pickup probe (not shown) as it scans across the top of chip 8.

In FIG. 2B, line 12 is a graphical representation of the intensity of received acoustic energy by the scanning pickup probe versus the distance across chip 8 through pathway 10. Similarly, in FIG. 2C, line 13 represents the intensity of received energy by the scanning pickup probe as it crosses chip 8 along pathway 11. In comparison to the constant slope of line 12, line 13 has a change or discontinuity in the energy received at point 14, which represents the point where the scanning pickup probe crosses crack 9.

Of course, these figures only represent received energy in one axis. However, because sound energy propagates in all three axes, the present invention is capable of analyzing the received signal in the x, y and z axes.

Figure 3:
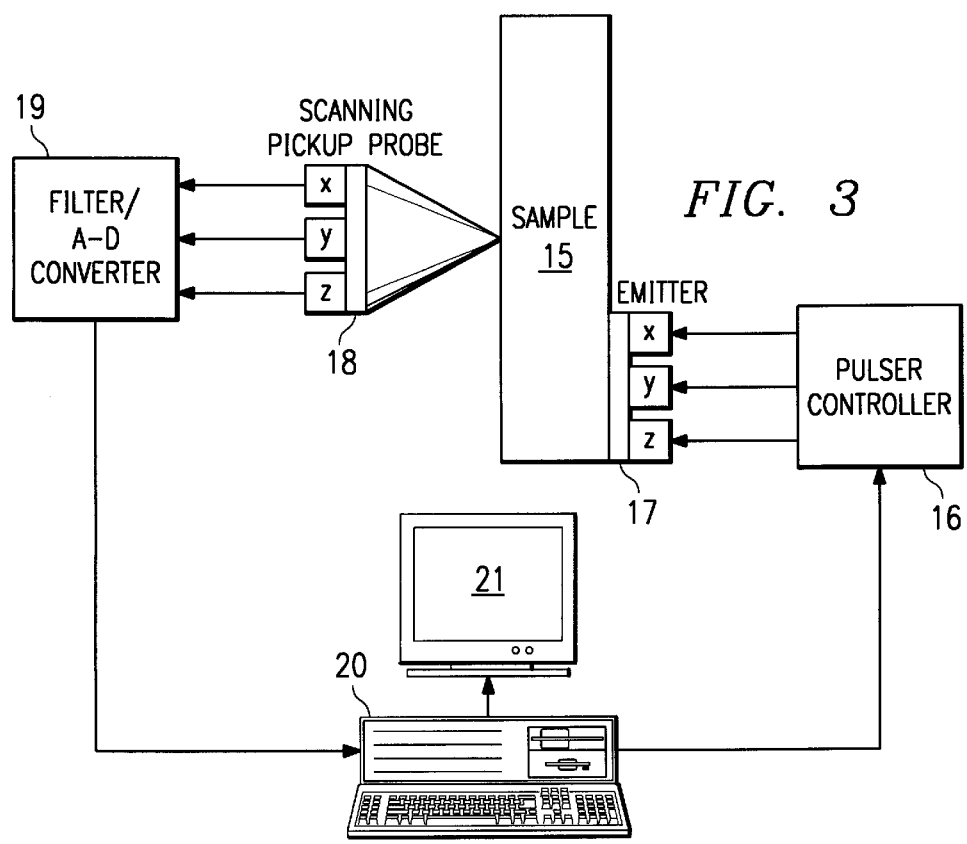
FIG. 3 is a schematic diagram of the apparatus for detecting flip-chip die cracks.

FIG. 3 shows a block diagram of the apparatus for detecting cracks in a flip-chip die. Emitter 17 produces the acoustic energy that is sent through the chip 15 sample. The present invention allows for several types of energy waves, including but not limited to: sine waves, square waves, and triangular waves. Also, the acoustic energy waves can be sent in either continuous or discrete pulse fashion. Furthermore, the present invention allows for a mixing of the acoustic energy wave types in order to facilitate analysis of chip 15.

Scanning pickup probe 18 perceives the acoustic energy after it is transmitted through chip 15. Just as emitter 17 can transmit acoustic energy in three axes, scanning pickup probe 18 is capable of receiving this energy in all three axes. One embodiment of the invention allows first for emitter 17 to transmit in the x axis, and then the scanning pickup probe 18 "looks" for energy in all three axes: x, y and z. Emitter 17 then transmits in the y axis, whereupon scanning pickup probe 18 again looks in all three axes. Finally, emitter 17 transmits in the z axis, and then scanning pickup probe 18 receives energy in all three axes.

After scanning pickup probe 18 receives the inputs of acoustic wave energy from chip 15, this energy is then processed through analog to digital converter 19, where the energy signal is filtered and converted into an electrical digital signal. This digital signal is then sent to computer 20 which processes the information in order to create a visual image which it transmits to display 21.

One embodiment of the present invention creates a visual image based upon different colors which represent different density readings of chip 15. For example, the color red could be used for a standard density of a chip, and blue used for the density of a crack (i.e., which is the density of air).

Computer 20 is also connected to pulser controller 16. Pulser controller 16 acts as a digital to analog converter, as it receives digital signals from computer 20 which are then converted into an analog signal in order to control emitter 17. Pulser controller 16 controls the various factors for the type of acoustic energy wave that is created. These include the amplitude, timing, frequency, as well as the phase of the energy wave. Also, pulser controller 16 applies any damping that is necessary in order to fully optimize the acoustic energy signal.

Generally, the present invention allows for emitter 17 to produce frequencies with ranges of approximately 1 MHZ to 250 MHZ. Frequencies that are useful for the plastic encapsulated chips include 10 MHZ to 75 MHZ, while the ceramic flip-chips generally require frequencies in the range of 75 MHZ up to as high as 300 MHZ. One embodiment of the invention operates in the 150 MHZ to 200 MHZ range.

Filter and analog to digital converter 19 amplifies the received energy wave from scanning pickup probe 18, and then breaks the signal down into different frequencies in the spectrum. This energy signal is then converted to digital form and sent to computer 20 for analysis.

In another embodiment of the present invention, laser light energy can be used instead of acoustic energy in the detection of cracks in flip-chip dies. This laser energy would be produced by a laser source and reflected off of the chip sample. This reflected energy is then received by a photo detector device, where frequency and phase analysis can be undertaken.

The present invention has been described in detail, it should be understood that various changes, substitutions and alterations can be made hereto without departing from the scope of the invention as defined by the appended claims.

What is claimed is:

1. An apparatus for detecting cracks in a flip-chip die, comprising:

an emitter coupled to the die at a fixed position for emitting acoustic energy into said die along a first axis;

a movable probe located on the die at a selectable position for receiving the acoustic energy; and a device coupled to the movable probe for detecting the acoustic energy along the first axis.

2. The apparatus of claim 1, wherein the emitter transmits the acoustic energy in compression wave pulses.

3. The apparatus of claim 1, wherein the emitter emits energy along a second and a third axis, the second axis being perpendicular to the first axis, the third axis being perpendicular to the first axis and the second axis, and the device for detecting the received energy can detect energy along the second axis and the third axis.

4. The apparatus of claim 1, wherein:

said movable probe is of a type similar to a phonographic needle pickup having a needle in contact with said flip-chip die.

5. The apparatus of claim 1, wherein:

said flip-chip die is a plastic encapsulated chip; and said emitter generates acoustic energy in the frequency range of 10 MHZ to 75 MHZ.

6. The apparatus of claim 1, wherein:

said flip-chip die is a ceramic flip-chip; and said emitter generates acoustic energy in the frequency range of 75 MHZ to 300 MHZ.

7. A method for detecting cracks in a flip-chip die, comprising the steps of:

emitting acoustic energy from an emitter coupled to the die at a fixed position along a first axis;

receiving the energy with a movable probe located on the die at a selectable position; and detecting the acoustic energy with a device coupled to the movable probe along the first axis.

8. The method of claim 7, further comprising the steps of:

emitting energy from the emitter along a second axis and a third axis, the second axis being perpendicular to the first axis, the third axis being perpendicular to the first axis and to the second axis;

receiving the energy with the probe along the second axis and the third axis; and detecting the energy with a device along the second axis and the third axis.

9. The method of claim 7, wherein the step of emitting acoustic energy emits acoustic energy in compression wave pulses.

10. The method of claim 7, wherein:

said step of receiving the energy with a movable probe includes a movable probe is of a type similar to a phonographic needle pickup having a needle in contact with said flip-chip die.

11. The method of claim 7, wherein the flip-chip die is a plastic encapsulated chip, said method wherein:

said step of emitting acoustic energy from an emitter generates acoustic energy in the frequency range of 10 MHZ to 75 MHZ.

12. The method of claim 7, wherein the flip-chip die is a ceramic flip-chip, said method wherein:

said step of emitting acoustic energy from an emitter generates acoustic energy in the frequency range of 75 MHZ to 300 MHZ.

13. The method of claim 7, further comprising:

scanning the movable probe along the flip-chip die; and indicating a crack in the flip-chip die at a point of the movable probe upon a discontinuity in said detected acoustic energy.

14. A system for detecting cracks in a flip-chip die, comprising:

an emitter coupled to the die at a fixed position for emitting acoustic energy through the die;

a movable probe located on the die at a selectable position for receiving the acoustic energy;

a device coupled to the movable probe for detecting the acoustic energy;

a filter and analog to digital converter coupled to the device for detecting the acoustic energy for processing the energy into various sections of the frequency spectrum and for converting the energy from an analog form into a digital signal; and a controller coupled to the emitter for controlling the amplitude, timing, frequency and phase of the energy.

15. The system of claim 14, wherein the emitter transmits the acoustic energy in compression wave pulses.

16. The system of claim 14, wherein:

said movable probe is of a type similar to a phonographic needle pickup having a needle in contact with said flip-chip die.

17. The system of claim 14, wherein:

said flip-chip die is a plastic encapsulated chip; and said emitter generates acoustic energy in the frequency range of 10 MHZ to 75 MHZ.

18. The system of claim 14, wherein:

said flip-chip die is a ceramic flip-chip; and said emitter generates acoustic energy in the frequency range of 75 MHZ to 300 MHZ.

* * * * *